(12) United States Patent
Kalnas et al.

(10) Patent No.: US 7,184,962 B2
(45) Date of Patent: Feb. 27, 2007

(54) SYSTEM AND METHOD FOR MANAGING EMPLOYEE ABSENCES

(75) Inventors: Patrick J. Kalnas, McDonald, PA (US); Steven A. Scherm, Irwin, PA (US)

(73) Assignee: KCRS, Inc., Cranberry Township, PA (US)

( * ) Notice: Subject to any disclaimer, the term of this patent is extended or adjusted under 35 U.S.C. 154(b) by 0 days.

(21) Appl. No.: 10/365,814

(22) Filed: Feb. 13, 2003

(65) Prior Publication Data

US 2003/0154098 A1  Aug. 14, 2003

Related U.S. Application Data

(60) Provisional application No. 60/356,824, filed on Feb. 14, 2002.

(51) Int. Cl.
G06Q 99/00 (2006.01)

(52) U.S. Cl. .................. 705/1; 705/3; 705/7; 705/8; 705/9

(58) Field of Classification Search ............ 705/1, 705/3, 8, 9
See application file for complete search history.

(56) References Cited

U.S. PATENT DOCUMENTS

| | | | | |
|---|---|---|---|---|
| 5,842,182 | A * | 11/1998 | Bonner et al. ........... | 705/32 |
| 5,875,431 | A * | 2/1999 | Heckman et al. ........ | 705/7 |
| 6,065,000 | A * | 5/2000 | Jensen ..................... | 707/3 |
| 2002/0143595 | A1* | 10/2002 | Frank et al. ............. | 705/8 |
| 2003/0033184 | A1* | 2/2003 | Benbassat et al. ...... | 705/8 |
| 2003/0055691 | A1* | 3/2003 | Cooper et al. .......... | 705/7 |

FOREIGN PATENT DOCUMENTS

DE   3923524 A1 *  1/1991

OTHER PUBLICATIONS www.absence-mgr.com.*
www.corvel.com.*
www.knowledgepoint.com.*
www.workforcesoftware.com.*
www.sdssoftware.com.*
www.hrmsoftware.com.*
"Tracking absences on PCs." PC Week, v6, n47, p. 86(1), Nov. 27, 1989.*
Scicolone, Michael, "A documentation system worth viewing," HRMagazine, v38n2, pp. 34-38, Feb. 1993.*
"Information and control: asurvey of computerized systems," IRS Employment Review, n611, pp. 5-12, Jul. 1996.*
Reisenwitz, Eric M, "Absence/lost time management: Strategies to keep the workforce productive," Benefits Quarterly, v13n4, pp. 19-25, Fourth Quarter 1997.*
Kweller, Deborah S., "The emerging model of absence management." HR Focus, v75, n8, p. 9(2), Aug. 1998.*
"Three Specialty Companies Integrate Services to Offer Employer Total Absence Tracking and Disability Management." Business Wire, Jul. 19, 1999.*

(Continued)

*Primary Examiner*—Jonathan Ouellette
(74) *Attorney, Agent, or Firm*—Kirkpatrick & Lockhart Preston Gates Ellis LLP (57) ABSTRACT

A method for managing the absence of an employee is disclosed. The method includes generating an incident case related to the absence, defining portions of the incident case, and integrating the portions such that the incident case is accessible by one or more entities involved with managing the absence.

37 Claims, 4 Drawing Sheets

OTHER PUBLICATIONS

"Absence-Mgr.com Upgraded to Account for Family Medical Leave Act Requirements; Web-Based Tool Helps Employers to Better Manage Employee Absences," Business Wire, Feb. 16, 2000.*

"Corvel Launches Web-based Absence Management Tools."PR Newswire, Apr. 27, 2001.*

"Oracle Announces Immediate Availability of Oracle Time & Labor." PR Newswire, Sep. 21, 2001.*

"KnowledgePoint Enhances 'Virtual HR Department' Software to Give Small Business an Edge On Retention; People Manager 3.0 Tracks the Things That are Important to Employees." Business Wire, Oct. 4, 2001.*

Kweller, Deborah S., "The emerging modelof Absence management," HR Focus, v75n8, pp. 9-10, Aug. 1998.*

Lipold, Annmarie Geddes, "Managing the guy who isn't there." Business & Health, Nov. 2000.*

Ceniceros, Roberto, "CareMC.com; Award of Excellence in the Property/Casualty Claims Services category." Business Insurance, v35, p. 32, Oct. 8, 2001.* www.caremc.com, retrieved from Internet Archive Wayback Machine <www.archive.org >, applicable date ranges: Jun. 20, 2000-Jul. 26, 2001.*

"Corvel Announces CareMC Employer Website for Disability Management," PR Newswire, May 1, 2000.*

"Corvel Corporation Launches CareMC Marketsite." PR Newswire, Apr. 20, 2000.*

Ferguson, Tamels F, "The case for total absence management and integrates benefits," HR. Human Resource Planning, v24n3, pp. 36-46, 2001.*

* cited by examiner

SYSTEM AND METHOD FOR MANAGING EMPLOYEE ABSENCES

CROSS-REFERENCE TO RELATED APPLICATION

This application claims priority under 35 U.S.C. § 119(e) from provisional U.S. Patent Application Ser. No. 60/356,824 filed Feb. 14, 2002, which is incorporated herein by reference.

BACKGROUND

The present application is related, generally, to systems and methods for managing employee absences. As used herein, the term "absence" generally refers to a period of time that an employee is away from or restricted from fully performing the job normally performed by that employee, and the term "absence management" generally refers to the case management process for facilitating the employee's return to the job and includes the continuing management of the employees' status until all medical restrictions have been removed and the employee returns to full-duty.

An employee absence is typically triggered when an employee suffers an injury or illness. Such an injury or illness is commonly referred to as an incident. The costs associated with an employee absence incurred by an employer include both direct and indirect costs, and are directly correlated with the profitability of the employer. The direct costs include items such as insurance premiums, medical expenses, legal expenses, sick pay, disability income and administrative fees. The indirect costs include items such as lost productivity, overtime, replacement worker expenses, investigation expenses and decreased product quality. The costs associated with employee absences continue to escalate, and are estimated to exceed $1 trillion per year in the United States.

To improve profitability, employers have traditionally opted to focus the majority of their efforts on improving functions or departments that generate revenues, often devoting little or no attention to the practice of absence management. However, given the increasingly negative effect that employee absence costs are having on the bottom line of many employers, greater efforts are now being directed to proactively managing employee absences to reduce the costs associated therewith.

Although many employers now realize the strategic importance of absence management, the effective implementation of absence management has been relatively difficult. Absence management as currently practiced by many employers is a very fragmented, regulatory laden, form-burdened, manual process that involves a number of different entities. Such entities can include, for example, a case manager, human resource personnel, physicians, physical therapists, occupational therapists, attorneys, insurance carriers, third-party administrators, and governmental personnel. Absence management can require both extensive internal (e.g., department to department, employer to employee) and external (e.g., employer to physician, employer to attorney) communications, and each entity involved in the process can generate a great deal of information that collectively comprise the content of a particular case.

The fragmented absence management currently practiced by many employers is generally not conducive to effectively managing the case, accurately identifying the direct and indirect costs associated with the employee absence, or to compiling all of the information generated by the various entities. Employers are recognizing that it is extremely difficult to make good absence management decisions without knowing the actual costs associated with the employee absence or having access to the information generated by each entity involved in the process. Understandably, many employers are concluding that the absence management processes they currently follow are highly inefficient and relatively expensive to administer, and are not producing the desired level of improvement to the employer's profitability or the employee's care.

SUMMARY

In one general respect, the present invention is directed to a method for managing an absence of an employee. According to one embodiment, the method includes generating an incident case related to the absence, defining portions of the incident case, and integrating the portions such that the incident case is accessible by one or more entities involved with managing the absence. The method may also include populating a relational database with a plurality of parent files associated with one or more of the entities, and generating a report related to the absence.

In another general respect, the present invention is directed to a computer program stored on a computer readable medium. According to one embodiment, the computer program includes instructions to generate an incident case related to an absence of an employee, define portions of the incident case, and integrate the portions such that the incident case is accessible by one or more entities involved with managing the absence. The computer program may also include instructions to populate a relational database with a plurality of parent files associated with one or more of the entities, and generate a report related to the absence.

In another general respect, the present invention is directed to a system for managing an absence of an employee. According to one embodiment, the system includes means for generating an incident case related to the absence, means for defining portions of the incident case, and means for integrating the portions such that the incident case is accessible by one or more entities involved with managing the absence. The system may also include means for populating a relational database with a plurality of parent files associated with one or more of the entities, and means for generating a report related to the absence.

DESCRIPTION

It is to be understood that the figures and descriptions of the present invention have been simplified to illustrate elements that are relevant for a clear understanding of the present invention, while eliminating, for purposes of clarity, other elements. Those of ordinary skill in the art will recognize, however, that these and other elements may be desirable. However, because such elements are well known in the art, and because they do not facilitate a better understanding of the present invention, a discussion of such elements is not provided herein.

Figure 1:
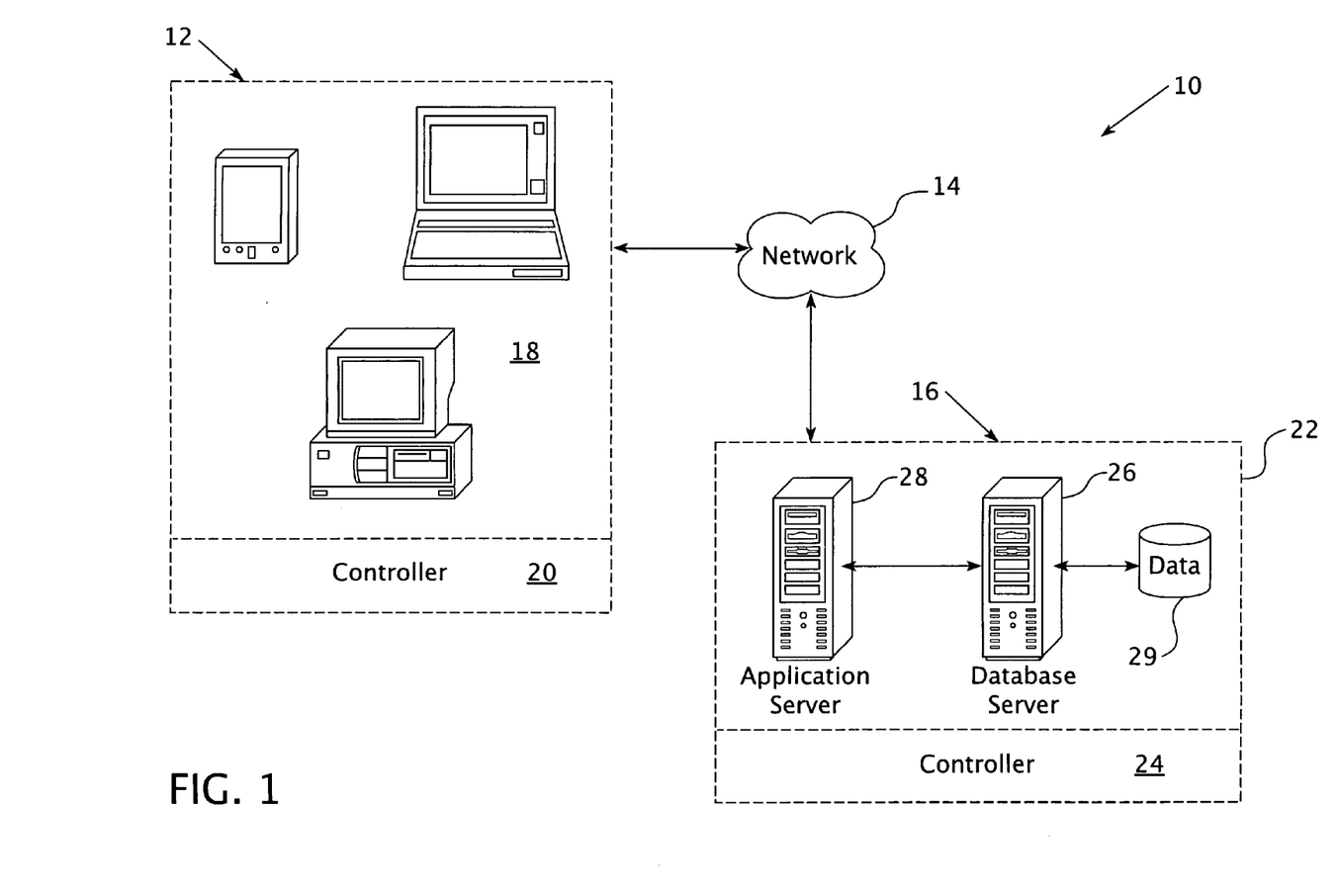
FIG. 1 illustrates one embodiment of a absence management system.

FIG. 1 illustrates one embodiment of an absence management system 10. The absence management system 10 may include a client system 12, a network 14, and a host system 16. The client system 12 and the host system 16 may be configured to communicate and exchange information with one another via the network 14. The absence management system 10 may be used to receive, integrate and present information associated with the absence of an employee, and such information may be utilized to make absence management decisions.

In general, the client system 12 may include a computer system having hardware and/or software components for communicating with the network 14 and the host system 16. The client system 12 may include one or more general-purpose computers (e.g., personal computers and/or servers), one or more special-purpose computers (e.g., devices specifically programmed to communicate with each other), or a combination of one or more general-purpose computers and one or more special-purpose computers. The client system 12 may be structured and arranged to communicate using various communication protocols (e.g., HTTP, TCP/IP, WAP, UDP) to establish connections between network elements and/or to operate within or in concert with one or more other systems such as, for example, the Internet and/or the World Wide Web (Web).

In one embodiment, the client system 12 may be implemented as a client device 18 operating under the command of a client controller 20. The broken lines shown surrounding the client controller 20 in FIG. 1 are intended to indicate that in some embodiments, the client controller 20, or portions thereof considered collectively, may instruct one or more elements of the client device 18 to operate as described.

According to one embodiment, the client device 18 may be implemented as a general-purpose computer capable of responding to and executing instructions in a defined manner. According to other embodiments, the client device 18 may be implemented as a special-purpose computer, a personal computer (PC), a workstation, a server, a laptop computer, a web-enabled telephone, a web-enabled personal digital assistant (PDA), a microprocessor, an integrated circuit, or any other component, machine, tool, equipment, or some combination thereof capable of responding to and executing instructions.

According to one embodiment, the client controller 20 may be implemented as a software application (e.g., operating system, browser application, client application, server application, proxy application, on-line service provider application, and/or private network application) installed on the client device 18 for directing communications. According to other embodiments, the client controller 20 may be implemented as a computer program, code, set of instructions, or some combination thereof, for independently or collectively instructing the client device 18 to interact and operate as programmed. The client controller 20 may be implemented utilizing any suitable computer language (e.g., Java, C or C++) and/or object-oriented techniques. According to another embodiment, the client controller 20 also may be implemented as a device, such as a workstation or PC, a microprocessor, a network server, a Java virtual machine, or an application-specific integrated circuit.

The client controller 20 may be embodied permanently or temporarily in any type of machine, component, physical or virtual equipment, storage medium, or propagated signal capable of delivering instructions to the client device 18. In particular, the client controller 20 (e.g., software application, computer program) may be stored on a storage medium (e.g., disk, device, or propagated signal), readable by a computer system, such that if the storage medium is read by the computer system, the functions described herein are performed.

According to one embodiment, the client system 12 may include a personal computer running a browser application. The client system 12 may display various graphical user interfaces (GUIs), such as Web pages, that request input from and deliver information to a user of the absence management system 10. For example, a system user may input requested information into a series of GUIs and then be presented with a display of absence management information.

The network 14 may include one or more delivery systems for directly or indirectly connecting the client system 12 and the host system 16. Examples of delivery systems include, but are not limited to, a local area network (LAN), a metropolitan area network (MAN), a wide area network (WAN), the Internet, the Web, a telephony network (e.g., analog, digital, wired, wireless, PSTN, ISDN, or xDSL), a radio network, a television network, a cable network, a satellite network, and/or any other wired or wireless communications network configured to carry data. Each network may include one or more elements, such as, for example, intermediate nodes, proxy servers, firewalls, routers, switches, adapters, sockets, and wired or wireless data pathways, configured to direct and/or deliver data.

In general, the host system 16 may include a computer system having hardware and/or software components for communicating with the network 14 and the client system 12. The host system 16 may include one or more general-purpose computers (e.g., personal computers and/or servers), one or more special-purpose computers (e.g., devices specifically programmed to communicate with each other), or a combination of one or more general-purpose computers and one or more special-purpose computers. The host system 16 may be structured and arranged to communicate using various communication protocols (e.g., HTTP, TCP/IP, WAP, UDP) to establish connections between network elements and/or to operate within or in concert with one or more other systems (e.g., the Internet and/or Web). The host system 16 may also include and/or form part of an information delivery network, such as, for example, the Internet, the Web, an on-line service provider, a private network, and/or any other analog or digital wired and/or wireless network that provides information.

In one embodiment, the host system 16 may include a host device 22 operating under the command of a host controller 24. The broken lines shown surrounding the host controller 24 in FIG. 1 are intended to indicate that in some implementations, the host controller 24, or portions thereof considered collectively, may instruct one or more elements of the host device 22 to operate as described. The host device 22 and the host controller 24 may be similar to the client device 18 and client controller 20 described hereinabove. Accordingly, the function of retrieving and displaying/printing absence management information may be implemented as software controlling one or more elements of the client system 12 and/or the host system 16.

As shown in FIG. 1, the host device 22 may include a database server 26 and an application server 28 in communication with the database server 26. The database server 26 may store data 29 such as, for example, absence management information, and such data 29 may be structured and organized as a relational database. The relational database may comprise a portion of a database management system, and the query language used for defining, maintaining, and viewing the absence management information in the relational database may be a structured query language (SQL).

The application server 28 may be configured to receive absence management information from the client system 12 via the network 14 and to present absence management information to the client system 12 via the network 14. The application server 28, which will be described in more detail hereinbelow with respect to FIG. 2, may also be configured to access various software applications, and the software applications may be stored at the application server 28 or elsewhere. It is to be understood that while the database server 26 and the application server 28 are shown in FIG. 1 as monolithic structures, each may include numerous elements (e.g., servers, routers, switches, firewalls, sockets, databases, tables, disks, hard drives, etc.) in various embodiments of the host system 16. For example, according to one embodiment, the application server 28 may include and/or form a part of a web server.

Figure 2:
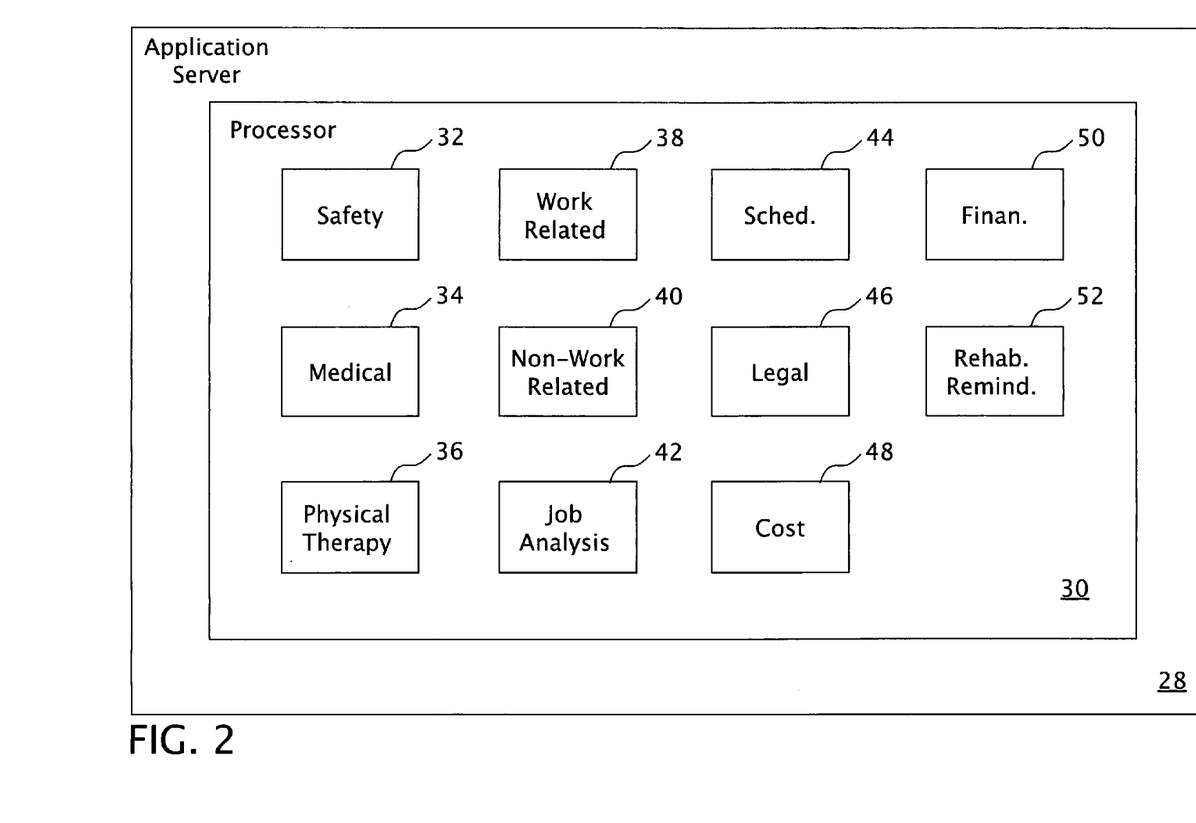
FIG. 2 illustrates one embodiment of an application server which comprises part of the absence management system of FIG. 1.

FIG. 2 illustrates one embodiment of the application server 28 of FIG. 1. In this embodiment, the application server 28 may include a processor 30. The processor 30 may be a central processing unit (CPU) including, e.g., a microprocessor, an application specific integrated circuit (ASIC), or one or more printed circuit boards. The application server 28 may also include one or more of the following modules: a safety module 32; a medical module 34, a physical therapy module 36, a work related module 38, a non-work related module 40, a job analysis module 42, a scheduler module 44, a legal module 46, a cost module 48, a financial module 50, and a rehabilitation reminder module 52. As used in the absence management method described hereinbelow, one or more of the modules 32-52 may function independently of one another, or may be fully integrated with each other. The application server 28 may also include any number of other modules such as, for example, an absence tracking module, a security module, a labor relations module, a wellness module, an environmental module and a risk management module. The application server 28 may also include a custom report writer module configured for use with the absence management system 10.

According to one embodiment, the modules 32–52 may be implemented, for example, as microcode configured into the logic of the processor 30, or may be implemented as programmable microcode stored in an electrically erasable programmable read only memory (EEPROM). According to another embodiment, the modules 32–52 may be implemented as software code to be executed by the processor 30. The software code may be written in any suitable programming language using any suitable programming technique. For example, the software code may be written in C using procedural programming techniques, or in Java or C++ using object-oriented programming techniques. The software code may be stored as a series of instructions or commands on a computer readable medium, such as a random access memory (RAM) or a read only memory (ROM), a magnetic medium such as a hard-drive or a floppy disk, or an optical medium such as a CD-ROM.

According to one embodiment, a number of the modules 32–52 may have built-in knowledge bases that detail best-practice case management procedures. The modules 32–52 may be configured to prompt a user of the absence management system 10 to access the built-in knowledge bases when appropriate. The modules 32–52 may also include an auditing feature that can track the access of the built-in knowledge bases by a user of the absence management system 10.

The safety module 32 may be used to record and modify certain details of an incident. The recorded details may include, for example, information concerning an accident, an illness, an injury type, an accident date, an accident location, an accident time, an accident witness and a treatment received. The recorded details define portions of an incident case, a compilation of information associated with an employee absence. The safety module 32 may also be used to generate reports such as, for example, injury reports, mandatory state reports, and OSHA (Occupational Safety and Health Administration) logs, needed to comply with various state and federal requirements.

The medical module 34 may be used to record and modify certain details of an employee's visit to a physician. The recorded details may include, for example, information concerning an attending physician, a treatment date, an injury diagnosis and a treatment plan. The recorded details define portions of an incident case. The medical module 34 may also be used to generate reports such as, for example, drug test reports and patient satisfaction reports.

The physical therapy module 36 may be used to record and modify certain details of an employee's visit to a physical therapist. The recorded details may include, for example, information concerning a primary therapist, an attending therapist, a therapy type, a therapy date and a physical therapy plan. The recorded details form portions of an incident case. The physical therapy module 36 may also be used to generate reports such as, for example, functional capacity evaluation reports.

The work related module 38 may be used to record and modify certain details of a workplace injury or illness suffered by an employee. The recorded details may include, for example, information concerning a work related claim, a claim date, a benefit amount, an employee contact date, a supervisor contact date and a physician contact date. The recorded details form portions of an incident case. The work related module 38 may also be used to generate reports such as, for example, reports showing whether an employee absence is work related or non-work related, reports showing the total number of work related and non-work related days of absence, reports showing the number of light duty cases and reports showing the number of lost time cases.

The non-work related module 40 may be used to record and modify certain details of a non-workplace injury or illness suffered by an employee. The recorded details may include, for example, information concerning a non-work related claim, a claim date, a benefit amount, an employee contact date, a supervisor contact date and a physician contact date. The recorded details form portions of an incident case. The non-work related module 40 may also be used to generate reports such as, for example, reports showing whether an employee absence is work related or non-work related, reports showing the total number of work related and non-work related days of absence, reports showing the number of light duty cases and reports showing the number of lost time cases.

The job analysis module 42 may be used to record and modify certain details of an employee's job. The recorded details may include, for example, information concerning a job title, a job function, a list of equipment used and a list of materials used. The recorded details define portions of an incident case. The job analysis module 42 may also be used to generate reports such as, for example, reports showing the primary functions and physical demands of a particular job.

The scheduler module 44 may be used to record and modify certain details of an employee's appointments associated with an absence. The recorded details may include, for example, information concerning a provider, a physician, a physical therapist, an appointment date, an appointment time and an appointment location. The recorded details define portions of an incident case. The scheduler module 44 may also be used to generate reports such as, for example, reports showing all the appointments scheduled for certain physicians.

The legal module 46 may be used to record and modify certain details of a legal case associated with an employee absence. One example of such a case would be a workers' compensation case. The recorded details may include, for example, information concerning an attorney name, an attorney phone number, a meeting date and a hearing date. The recorded details define portions of an incident case. The legal module 46 may also be used to incorporate documents such as, for example, photographs related to the legal case, with the incident case.

The cost module 48 may be used to record and modify certain details of the direct and indirect costs, including fixed and variable costs, associated with an employee absence. The recorded details may include, for example, information concerning an employee's salary, an insurance premium and a pay rate of a replacement worker. The recorded details define portions of an incident case.

The financial module 50 may be used to record and modify certain details associated with the fiscal management of an employee absence. The recorded details may include, for example, information concerning a bank name, an account number, an initial indemnity reserve amount, an initial legal reserve amount, an initial medical reserve amount, a transaction date and a transaction amount. The recorded details define portions of an incident case. The financial module 50 may also be used to generate reports such as, for example, reports showing account balances.

The rehabilitation module 52 may be used to assist disability management professionals by providing clinical definitions, illustrations, disability duration and treatment guidelines for illnesses and injuries. The rehabilitation module 52 may also be used to generate reports such as, for example, reports showing the ICD9 Code and the corresponding diagnosis for various inpatient or outpatient medical conditions.

Figure 3:
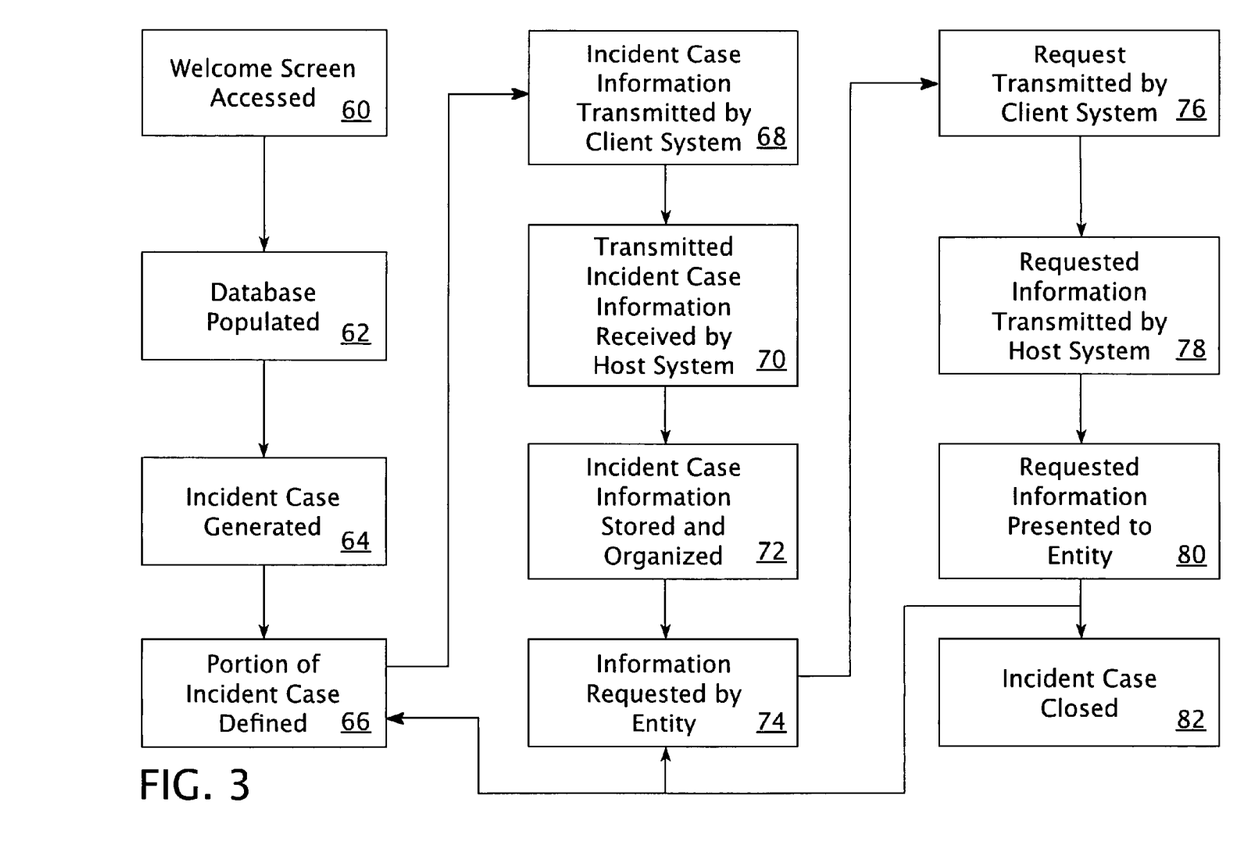
FIG. 3 illustrates one embodiment of a process flow through the absence management system of FIG. 1.
Figure 4:
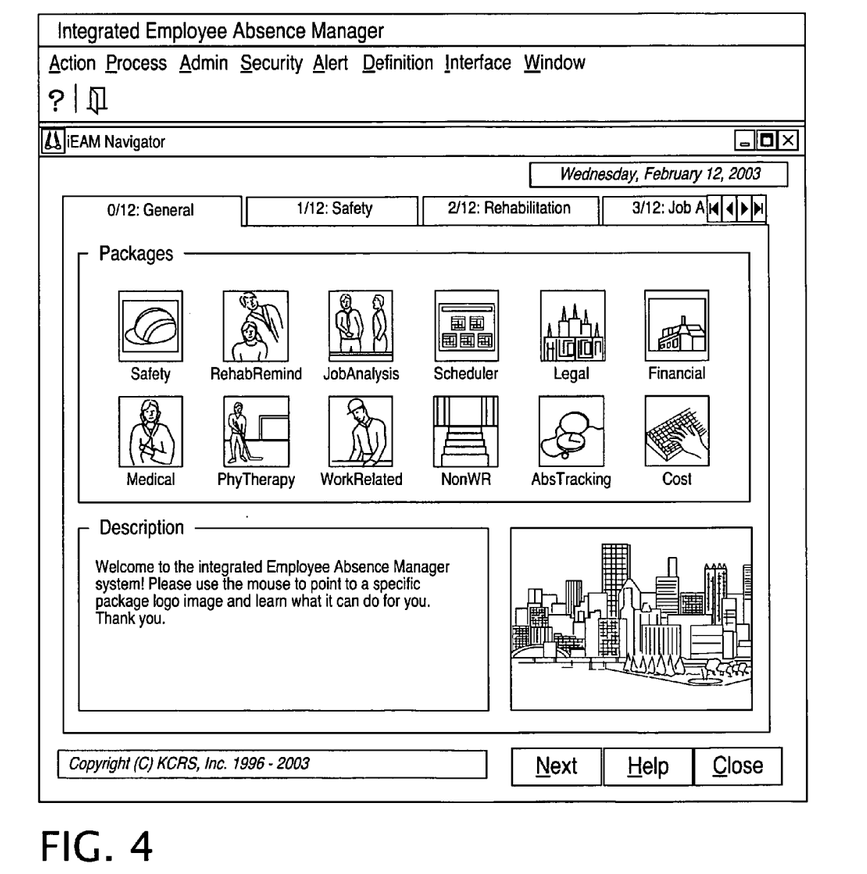
FIG. 4 illustrates one embodiment of a welcome screen generated by the absence management system of FIG. 1.

FIG. 3 illustrates one embodiment of a process flow through the absence management system 10 of FIG. 1. The absence/case management process flow begins at block 60, where one of the entities involved in the absence management process accesses a welcome screen generated by the absence management system 10 and displayed by the client system 12. An example of one embodiment of the welcome screen is shown in FIG. 4. From block 60, the process advances to block 62, where a relational database accessible by the database server 26 is populated with a plurality of parent files associated with one or more of the entities involved in the absence management process. The parent files may include employer information, employee information, medical provider information, insurance information, benefit information and union information. According to one embodiment, the information included in the parent files may be input to the absence management system 10 by selecting the "process" option shown in the menu bar of the welcome screen, then entering the requested information. According to another embodiment, file templates and application programming interfaces may be used to load bulk data from an external system to the absence management system 10. The application programming interfaces may also be used to transfer data from the absence management system 10 to one or more external systems.

From block 62, the process flow advances to block 64, where an incident case related to the employee absence is generated. According to one embodiment, the incident case may be generated by selecting the "safety" icon or the "medical" icon from the welcome screen, then selecting the "new incident case number" option. According to another embodiment, the incident case may be generated by selecting the "work related" icon, the "non-work related" icon, or the "physical therapy" icon from the welcome screen, then selecting the "new incident case number" option. From block 64, the process flow advances to block 66, where the various portions of the incident case are defined. The various portions of the incident case are defined by information input into the absence management system 10 via the client system 12. The information may be input throughout the life cycle of the employee absence by one or more of the entities involved in the absence management process. Collectively, the information input by one or more of the entities comprise the content of the incident case. According to one embodiment, the information may be input via graphical user interfaces created by one or more of the modules 32–50 described hereinabove and displayed by the client system 12.

From block 66, the process flow advances to block 68, where the client system 12 transmits the information to the host system 16 via the network 14. From block 68, the process flow advances to block 70, where the host system 16 receives the information transmitted from the client system 12. According to one embodiment, the transmitted information 12 may be received by the application server 28 described hereinabove. From block 70, the process advances to block 72, where the information defining the various portions of the incident case is stored and organized within a relational database. According to one embodiment, the information is accessible by the database server 26 described hereinabove and may also be stored at the database server 26.

From block 72, the process flow advances to block 74, where the one of the entities involved in the absence management process (e.g., a case manager) requests information from the absence management system 10. The request may be for information defining one or more portions of the incident case or it may be for one of the reports that can be generated by the absence management system 10. According to one embodiment, the request may be initiated by selecting an option from a graphical user interface displayed at the client system 12. From block 74, the process flow advances to block 76, where the client system 12 transmits the request to the host system 16 via the network 14.

From block 76, the process flow advances to block 78, where the host system 16 receives the request, processes the request, and transmits the requested information to the client system 12 via the network 14. From block 78, the process flow advances to block 80, where the client system 12 receives the requested information, processes the requested information, and presents the requested information to the entity. According to one embodiment, the requested information may be presented to the entity via a display monitor of the client system 12. According to another embodiment, the requested information may be presented to the entity via a printer of the client system 12.

From block 80, the process flow may return to block 66 or to block 74, where the process flow advances as described hereinabove, or the process flow may advance to block 82, where the incident case can be closed. According to one embodiment, the incident case may be closed by accessing the welcome screen, selecting the "administration" option shown in the menu bar, then selecting the "close incident" option.

With the assistance of the process described hereinabove, one or more of the entities involved in the absence/case management process may access all of the information associated with the employee absence, and may utilize the information in conjunction with the best-practice procedures incorporated in the modules 32–52 to make well-informed absence/case management decisions.

While several embodiments of the invention have been described, it should be apparent, however, that various modifications, alterations and adaptations to those embodiments may occur to persons skilled in the art with the attainment of some or all of the advantages of the present invention. It is therefore intended to cover all such modifications, alterations and adaptations without departing from the scope and spirit of the present invention as defined by the appended claims.

What is claimed is:

1. A computer-implemented method for managing an absence of an employee, the method comprising:
    generating an incident case related to the absence;
    defining portions of the incident case with a safety module, a medical module, a physical therapy module, a work related module, a non-work related module, a job analysis module, a scheduler module, a legal module, a cost module, and a financial module;
    integrating the portions such that all of the portions of the incident case are accessible by one or more entities involved with managing the absence; and
    determining a total cost associated with the absence.

2. The method of claim 1, wherein generating the incident case related to the absence includes generating the incident case for an employee injury.

3. The method of claim 1, wherein generating the incident case related to the absence includes generating the incident case for an employee illness.

4. The method of claim 1, wherein defining portions with the safety module includes defining one or more of an accident, an injury type, an accident date, an accident location, an accident time, an accident witness and a treatment received.

5. The method of claim 1, wherein defining portions with the medical module includes defining one or more of an attending physician, a treatment date, an injury diagnosis and a treatment plan.

6. The method of claim 1, wherein defining portions with the physical therapy module includes defining one or more of a primary therapist, an attending therapist, a therapy type, a therapy date and a physical therapy plan.

7. The method of claim 1, wherein defining portions with the work related module includes defining one or more of a work-related claim, a claim date, a benefit amount, an employee contact date, a supervisor contact date and a physician contact date.

8. The method of claim 1, wherein defining portions with the non-work related module includes defining one or more of a non-work related claim, a claim date, a benefit amount, an employee contact date, a supervisor contact date and a physician contact date.

9. The method of claim 1, wherein defining portions with the job analysis module includes defining one or more of a job title, a job function, a list of equipment used and a list of materials used.

10. The method of claim 1, wherein defining portions with the scheduler module includes defining one or more of a provider, a physician, a physical therapist, an appointment date, an appointment time and en appointment location.

11. The method of claim 1, wherein defining portions with the legal module includes defining an attorney name, an attorney phone number, a meeting date and a hearing date.

12. The method of claim 1, wherein defining portions with the cost module includes defining one or more of an employee salary, an insurance premium and a replacement worker expense.

13. The method of claim 1, wherein defining portions with the financial module includes defining a bank name, an account number, an initial indemnity reserve amount, an initial legal reserve amount, an initial medical reserve amount, a transaction date and a transaction amount.

14. The method of claim 1, wherein integrating the portions of the incident case includes organizing the portions within a relational database.

15. The method of claim 1, further comprising:
    populating a relational database with a plurality of parent files associated with one or more of the entities; and
    generating a report related to the absence.

16. The method of claim 15, wherein populating the relational database with the plurality of parent files includes populating the relational database with one or more of company information, employee information, medical provider information, insurance information, benefit information and union information.

17. The method of claim 15, wherein generating the report includes generating the report with one or more of the safety module, the medical module, the physical therapy module, the work related module, the non-work related module, the job analysis module, the scheduler module, the legal module, the cost module, and the financial module.

18. The method of claim 2, wherein generating the incident case for the employee injury includes generating the incident case for a non-work related injury.

19. The method of claim 3, wherein generating the incident case for the employee illness includes generating the incident case for a non-work related illness.

20. The method of claim 1, wherein determining the total cost associated with the absence includes determining direct and indirect costs associated with the absence.

21. The method of claim 20, wherein determining the total cost associated with the absence includes determining fixed and variable costs associated with the absence.

22. A system for managing an absence of an employee, the system comprising:
    means for generating an incident case related to the absence;
    means for defining portions of the incident case, wherein the means for defining portions of the incident case include a client system and a host system in communication with the client system, the host system comprising a database server and an application server in communication with the database server, the application server including a safety module, a medical module, a physical therapy module, a work related module, a non-work related module, a job analysis module, a scheduler module, a legal module, a cost module arid a financial module;

means for integrating the portions such that all of the portions of the incident case are accessible by one or more entities involved with managing the absence; and means for determining a total cost associated with the incident case.

23. The system of claim 22, wherein the means for generating the incident case related to the absence include the client system and the host system in communication with the client system.

24. The system of claim 22, wherein the means for integrating the portions include the host system.

25. The system of claim 22, further comprising:
means for populating a relational database with a plurality of parent files associated with one or more of the entities; and
means for generating a report related to the absence.

26. The system of claim 22, further comprising means for determining direct and indirect costs associated with the incident case.

27. The system of claim 26, further comprising means for determining fixed and variable costs associated with the incident case.

28. The system of claim 22, wherein the safety module records information including one or more of an accident, an injury type, an accident date, an accident location, an accident time, an accident witness and a treatment received.

29. The system of claim 22, wherein the medical module records information including one or more of an attending physician, a treatment date, an injury diagnosis and a treatment plan.

30. The system of claim 22, wherein the physical therapy module records information including one or more of a primary therapist, an attending therapist, a therapy type, a therapy date and a physical therapy plan.

31. The system of claim 22, wherein the work related module records information including one or more of a work-related claim, a claim date, a benefit amount, an employee contact date, a supervisor contact date and a physician contact date.

32. The system of claim 22, wherein the non-work related module records information including one or more of a non-work related claim, a claim date, a benefit amount, an employee contact date, a supervisor contact date and a physician contact date.

33. The system of claim 22, wherein the job analysis module records information including one or more of a job title, a job function, a list of equipment used and a list of materials used.

34. The system of claim 22, wherein the scheduler module records information including one or more of a provider, a physician, a physical therapist, an appointment date, an appointment time and an appointment location.

35. The system of claim 22, wherein the legal module records information including one or more of an attorney name, an attorney phone number, a meeting date and a hearing date.

36. The system of claim 22, wherein the cost module records information including one or more of an employee salary, an insurance premium and a replacement worker expense.

37. The system of claim 22, wherein the financial module records information including one or more of a bank name, an account number, an initial indemnity reserve amount, an initial legal reserve amount, an initial medical reserve amount, a transaction date and a transaction amount.

* * * * *

UNITED STATES PATENT AND TRADEMARK OFFICE
CERTIFICATE OF CORRECTION

PATENT NO. : 7,184,962 B2
APPLICATION NO. : 10/365814
DATED : February 27, 2007
INVENTOR(S) : Patrick J. Kalnas et al.

It is certified that error appears in the above-identified patent and that said Letters Patent is hereby corrected as shown below:

Column 10, line 8, delete "en" and replace therewith --an--.

Column 10, line 66, delete "arid" and replace therewith --and--.

Signed and Sealed this

Fourth Day of November, 2008

JON W. DUDAS
*Director of the United States Patent and Trademark Office*